(12) United States Patent
Feikert et al.

(10) Patent No.: US 7,292,029 B2
(45) Date of Patent: Nov. 6, 2007

(54) METHOD FOR DETECTING SUBSTRUCTURE

(75) Inventors: Edward E. Feikert, St. Charles, MO (US); Nancy Wood, Clayton, MO (US); Eugene A. Myers, St. Charles, MO (US)

(73) Assignee: The Boeing Company, Chicago, IL (US)

( * ) Notice: Subject to any disclaimer, the term of this patent is extended or adjusted under 35 U.S.C. 154(b) by 253 days.

(21) Appl. No.: 10/975,328

(22) Filed: Oct. 28, 2004

(65) Prior Publication Data

US 2006/0091880 A1 May 4, 2006

(51) Int. Cl.
*G01N 27/82* (2006.01)
*G01R 33/02* (2006.01)

(52) U.S. Cl. .................. 324/240; 324/228; 324/262

(58) Field of Classification Search ............... 324/240, 324/228, 262
See application file for complete search history.

(56) References Cited

U.S. PATENT DOCUMENTS

| | | | |
|---|---|---|---|
| 2,785,592 | A | 3/1957 | Caples et al. |
| 4,774,842 | A | 10/1988 | Kollar et al. |
| 5,833,799 | A | 11/1998 | Mittleider |
| 2003/0192382 | A1 | 10/2003 | Mueller |
| 2003/0212489 | A1* | 11/2003 | Georgeson et al. ............. 702/1 |
| 2004/0036042 | A1 | 2/2004 | Drake |

OTHER PUBLICATIONS

Brochure "MAUS V" The Boeing Company, St. Luis, USA.
Marsh, G., "Finding flaws in composites", Reinforced Platics, Elsevier Advanced Technology, Dec. 2002, pp. 42-46, vol. 46, No. 12, New York, NY, US.
European search report dated Feb. 16, 2006.
Brochure "MAUS V" The Boeing Company, St. Luis, USA, Date Unknown.

* cited by examiner

*Primary Examiner*—Reena Aurora
(74) *Attorney, Agent, or Firm*—Ingrassia Fisher & Lorenz, P.C.

(57) ABSTRACT

A method for detecting substructure includes the steps of: nondestructively scanning an assembly using a substructure scanning system including a precision motion carriage and a nondestructive scanning sensor, positioning the assembly under the substructure scanning system, positioning the scanning sensor on the outer skin, moving the scanning sensor over the outer skin with the precision motion carriage, locating the substructure through the outer skin, and controlling an assembly process using the location of the substructure. By using the method of the present invention substructure features may be located through an outer skin with sufficient accuracy to control assembly operations and to meet engineering tolerances. The method for precisely detecting substructure using precision eddy current scanning may be used for, but is not limited to, the location of substructure features, such as edges of flanges, machined steps, or tooling holes, covered by outer mold line skins of an aircraft airframe.

10 Claims, 6 Drawing Sheets

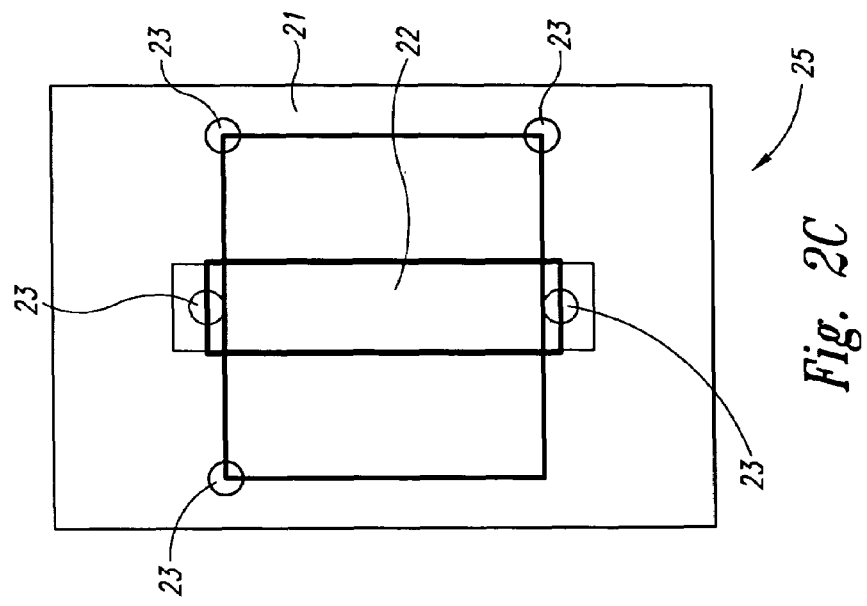
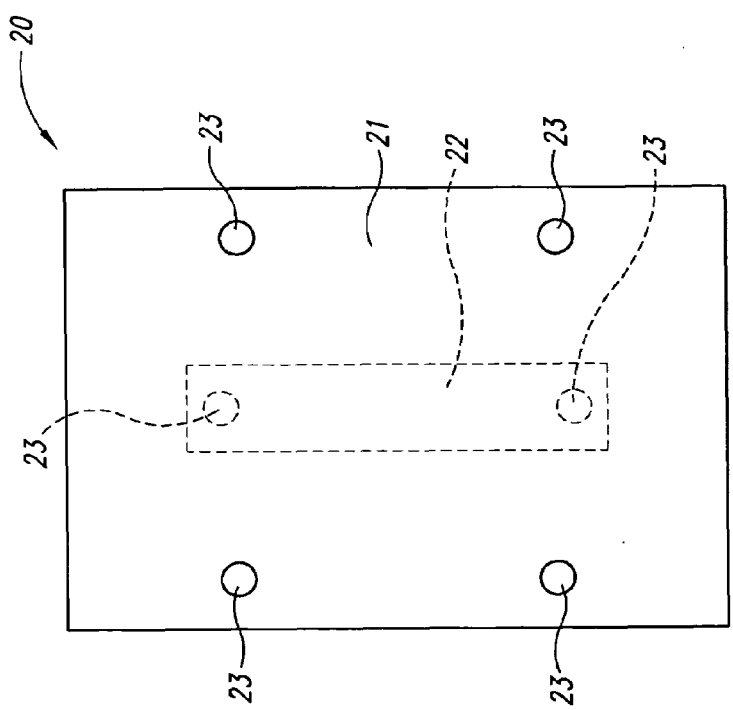
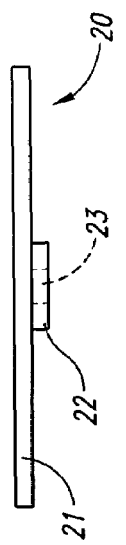

METHOD FOR DETECTING SUBSTRUCTURE

BACKGROUND OF THE INVENTION

The present invention generally relates to nondestructive inspection methods and, more particularly, to detecting substructure using precision eddy current scanning.

Automated assembly systems in the aerospace industry, for example, for airframe assembly of aircraft, generally employ some type of vision system for locating structure components and key features of components, such as edges of flanges, machined steps, and tooling holes. Knowledge of the exact location of these features is necessary, since these features are used to adjust numerically controlled programs for drilling holes or other machining operations, such as trimming or reaming, to maintain blueprint tolerances. Currently, it is often necessary to manually record where the substructure is located. In order to do this, the outer mold line skins, for example of a section of the fuselage or the wing, need to be removed to make the substructure underneath visible. Once a map of the substructure is created, the outer mold line skins are temporarily fastened to the structure and the created map of the substructure needs to be transferred to the skin. Since this step is performed while the assembly is in the machine bed, the flow time is impacted and the percentage of the machine time actually used for the intended function, such as drilling, is reduced.

Eddy current as a nondestructive inspection process is commonly used in the aerospace industry to detect subsurface flaws or anomalies in conductive materials. The advantage of eddy current for nondestructive inspection is the ability to perform scanning through the outer skin material. Eddy current data can be collected using automated scanning systems to improve the quality of the measurements and to construct images of scanned areas. The most common type of scanning is line scanning where an automated system is used to push the probe at a fixed speed. The data is usually presented as a strip chart recording. The advantage of using a linear scanning system is that the probe is moved at a constant speed such that an indication on the strip chart can be correlated to a position on the part being scanned. Two-dimensional scanning systems are used to scan a two-dimensional area. This could be a scanning system that scans over a relatively flat area in an x-y raster mode. The data is typically displayed in a C-scan, which is a false-color plot of signal strength or phase angle shift as a function of position. Mobile automated scanners, such as MAUS® IV and V developed by The Boeing Company, St. Louis, are generally used in the aerospace industry for nondestructive testing utilizing eddy current and ultrasonic waves. MAUS IV eddy current C-scans are used, for example, for corrosion detection or crack detection around fastener holes.

As can be seen, there is a need for a method to accurately and effectively locate and map the substructure features of an aircraft airframe that are located underneath the outer mold line skins. Furthermore, there is a need to eliminate the step of the outer skin removal in order to see the substructure and the step of skin installation after recording the substructure. Still further, there is a need to improve the product flow and automation of aircraft assemblies.

There has, therefore, arisen a need to provide a method for detecting substructure using nondestructive techniques. There has further arisen a need to locate substructure features with sufficient accuracy to control assembly operations and meet engineering tolerances. There has still further arisen a need to provide a device that allows detection and location of substructure features within the tolerances required.

SUMMARY OF THE INVENTION

The present invention provides for precisely detecting substructure using precision eddy current scanning. The present invention further provides a precision motion carriage that enables the location of substructure features within the engineering tolerances required. The present invention still further provides a method for the location of substructure features through an outer panel with sufficient accuracy to control assembly operations that may be used for, but is not limited to, the location of substructure features, such as edges of flanges, machined steps, or tooling holes, covered by outer mold line skins of an aircraft airframe.

In one aspect of the present invention, a method for detecting substructure comprises the steps of: nondestructively scanning an assembly using a substructure scanning system including a precision motion carriage and a nondestructive scanning sensor; positioning the assembly including a substructure covered with an outer skin under the substructure scanning system; positioning the scanning sensor on the outer skin of the assembly; moving the scanning sensor over the outer skin with the precision motion carriage; locating the substructure through the outer skin by evaluating signals received from the scanning sensor to locate the substructure; and controlling an assembly process using the location of the substructure.

In another aspect of the present invention, a method for precisely positioning and moving a probe comprises the steps of: enclosing a two-dimensional area using a frame; inserting a first probe positioner including a first opening into the frame; inserting a second probe positioner including a second opening into the frame; forming a window with the first opening and with the second opening; inserting a probe into the window; using the first probe positioner and the second probe positioner to accurately position the probe on the two-dimensional area; and using the first probe positioner and the second probe positioner to accurately move the probe across the two-dimensional area in an x-y raster mode. The first probe positioner is movable in y-direction within the frame. The first probe positioner is movable in x-direction within the frame. The second probe positioner is located above the first probe positioner.

In still another aspect of the present invention, a method for detecting substructure of an aircraft wing comprises the steps of: scanning an aircraft wing using a gantry motion system including a gantry, a bar, a pole, and an eddy current scanning sensor; inserting the bar into the gantry extending in y-direction across the gantry and being movable in x-direction; attaching the pole to the bar; attaching the eddy current scanning sensor to the pole; positioning the aircraft wing including a substructure covered with outer mold line skins under the gantry; moving the eddy current scanning sensor towards the wing; positioning the eddy current scanning sensor on the outer mold line skin of the wing; moving the eddy current scanning sensor over the outer mold line skin in an x-y raster mode; locating the substructure through the outer skin; and controlling a numerically controlled assembly process using the location of the substructure. The pole is movable in y-direction along the bar and in z-direction.

In a further aspect of the present invention, an assembly process comprises the steps of: fitting outer skins on a substructure to form an assembly; moving the assembly to a assembly machine; loading a substructure scanning system into the machine; activating the substructure scanning system; executing scanning programs; obtaining and saving scan point data; deactivating and removing the substructure scanning system; executing numerically controlled programs for the machine; using the scan point data to correct points and to align the assembly relative to machining tools of the machine; completing all numerically controlled programs with the machine; and removing the assembly from the assembly machine.

In still a further aspect of the present invention, a method for machine coordinate correction comprises the steps of: sending a correction request from an assembly machine to a substructure scanning system; positioning an eddy current scanning sensor on the outer skin of an assembly using the substructure scanning system; moving the eddy current scanning sensor over the outer skin of the assembly using the substructure scanning system; collecting scanning sensor data each time the eddy current scanning sensor is moved by a small increment; compiling a data file containing position information and the scanning sensor data; analyzing the data file to identify features of a substructure located underneath the outer skin; computing coordinates of the assembly machine to identify location of the substructure features relative to the assembly machine position; and returning machine coordinates orienting the assembly machine relative to the substructure features.

In still another aspect of the present invention, a gantry motion system comprises a gantry covering a two-dimensional area, a bar inserted into the gantry, a pole attached to the bar, and a probe attached to the pole. The bar extends in y-direction across the gantry and wherein the bar is movable in x-direction. The pole is movable horizontally in y-direction along the bar and vertically in z-direction.

These and other features, aspects and advantages of the present invention will become better understood with reference to the following drawings, description and claims.

BRIEF DESCRIPTION OF THE DRAWINGS

FIG. 2a is a top view of a test specimen according to one embodiment of the present invention;

FIG. 2b is a side view of a test specimen according to one embodiment of the present invention;

FIG. 2c is a C-scan of a test specimen according to one embodiment of the present invention;

DETAILED DESCRIPTION OF THE INVENTION

Figure 1:
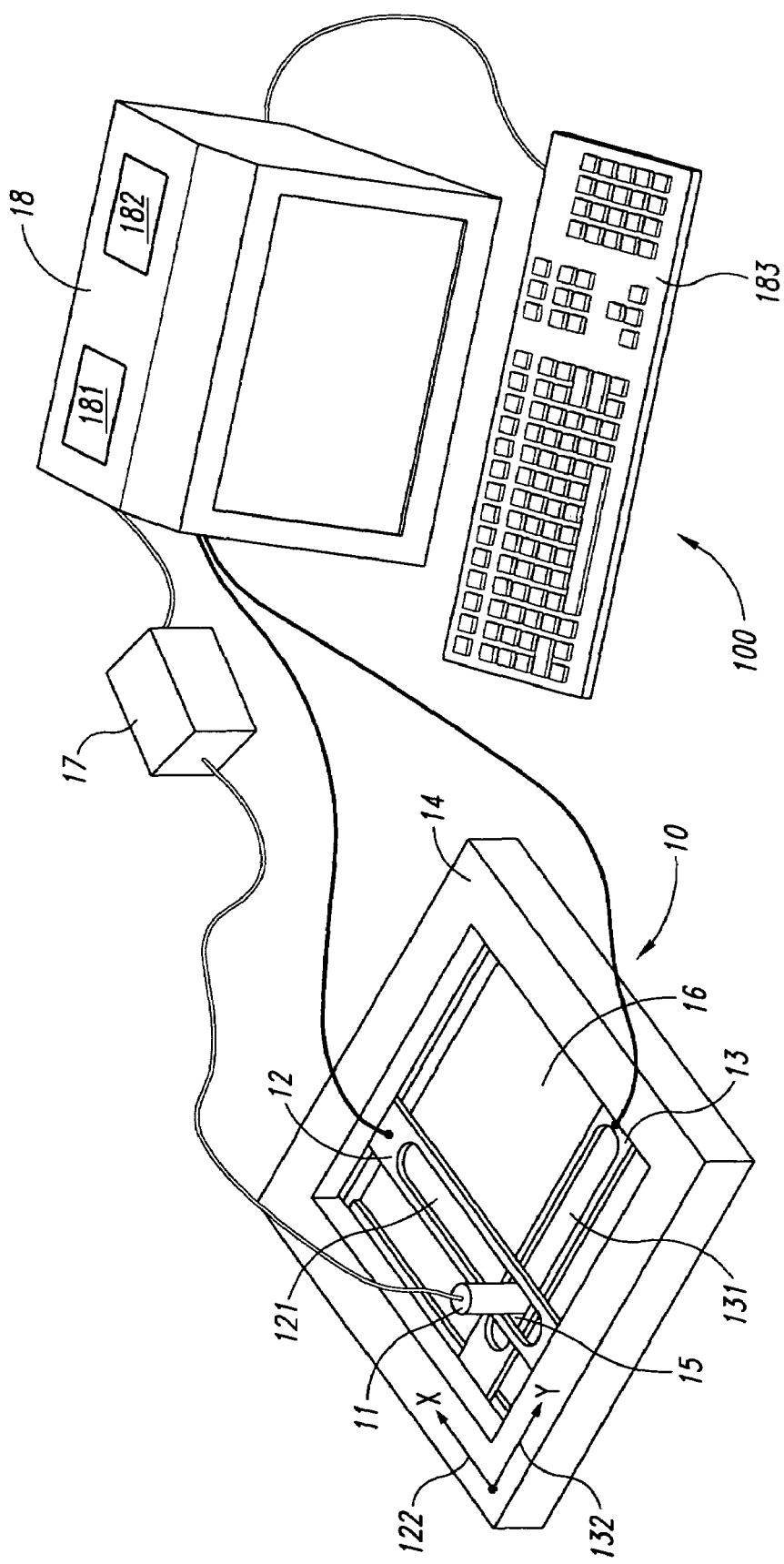
FIG. 1 is a schematic view of a dependent scanning system according to one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides for detecting substructure using nondestructive techniques. Contrary to the known prior art, an outer panel does not need to be removed to scan substructure that lies underneath the panel. Furthermore, by using the method for detecting substructure according to one embodiment of the present invention, substructure features can be located through the skin of a structure with sufficient accuracy to control assembly operations and meet engineering tolerances, which is not possible using prior art handheld devices or prior art nondestructive techniques. The method for detecting substructure as in one embodiment of the present invention may be used in the aerospace industry, for example, in the airframe assembly of aircraft. The method for detecting substructure further enables detection and location of substructure features, such as edges of flanges, machined steps, or tooling holes, that are located underneath the outer mold line skins, for example, of a fuselage or a wing of an aircraft.

In one embodiment, the present invention uses eddy current to scan the outer mold line skin of an aircraft in order to detect substructure features underneath the skin. Since the removal of the skin is no longer required to create a map of the substructure, the steps of removing and refastening the skin, as currently needed using prior art methods, can be eliminated. Furthermore, by using eddy current for scanning a solid sheet of metallic or nonmetallic material, such as an aircraft airframe skin, edges and other features of metallic substructure located underneath the skin, on the side of the skin opposite to the scanning probe, can be located without removal of the airframe skin and in a nondestructive process. The advantage of eddy current for scanning is its ability to perform the scanning through the outer skin material. This will allow the temporary installation step for the outer mold line skins, for example, for a aircraft fuselage or wing, to take place before the assembly is presented to an automated machining system, for example, an automated drilling system, and will eliminate the intermediate step of skin installation after scanning as needed with prior art scanning methods. Using prior art scanning methods, the location of the substructure and the step of temporary fastening is performed while the assembly is situated in the machine bed.

In one embodiment, the present invention provides a precision motion carriage that enables application of the eddy current scanning process with a high accuracy. By using the precision motion carriage as in one embodiment of the present invention, substructure features can be located with sufficient accuracy to control assembly operations, for example, numerically controlled programs for drilling holes, for trimming, or for reaming, and to meet engineering tolerances. Using prior art hand-held devices for detecting substructure does not provide this accuracy.

In one embodiment, the present invention provides a gantry motion system that moves the scanning sensor precisely over an area to be examined. In another embodiment, the present invention provides a robot motion system that moves the scanning sensor precisely over an area to be examined. Both motion systems enable the integration of the eddy current scanning process as in one embodiment of the present invention into numerically controlled machines, such as numerically controlled drilling machines, and, therefore, reduce the machine bed low time. Furthermore, the integration of the scanning process into the numerically controlled machining process enables instant machine coordinate correction without the need for manual actions, which provides more flexibility in the assembly process than prior art methods where the skins needs to be removed before the substructure features are visible, and where a map of the substructure needs to be created manually. Consequently, by using the method for detecting substructure using eddy current scanning as in one embodiment of the present invention, the product flow and automation of aircraft assemblies can be improved and the need for subassemblies and components can be reduced in comparison with prior art methods for locating substructure.

Figure 3:
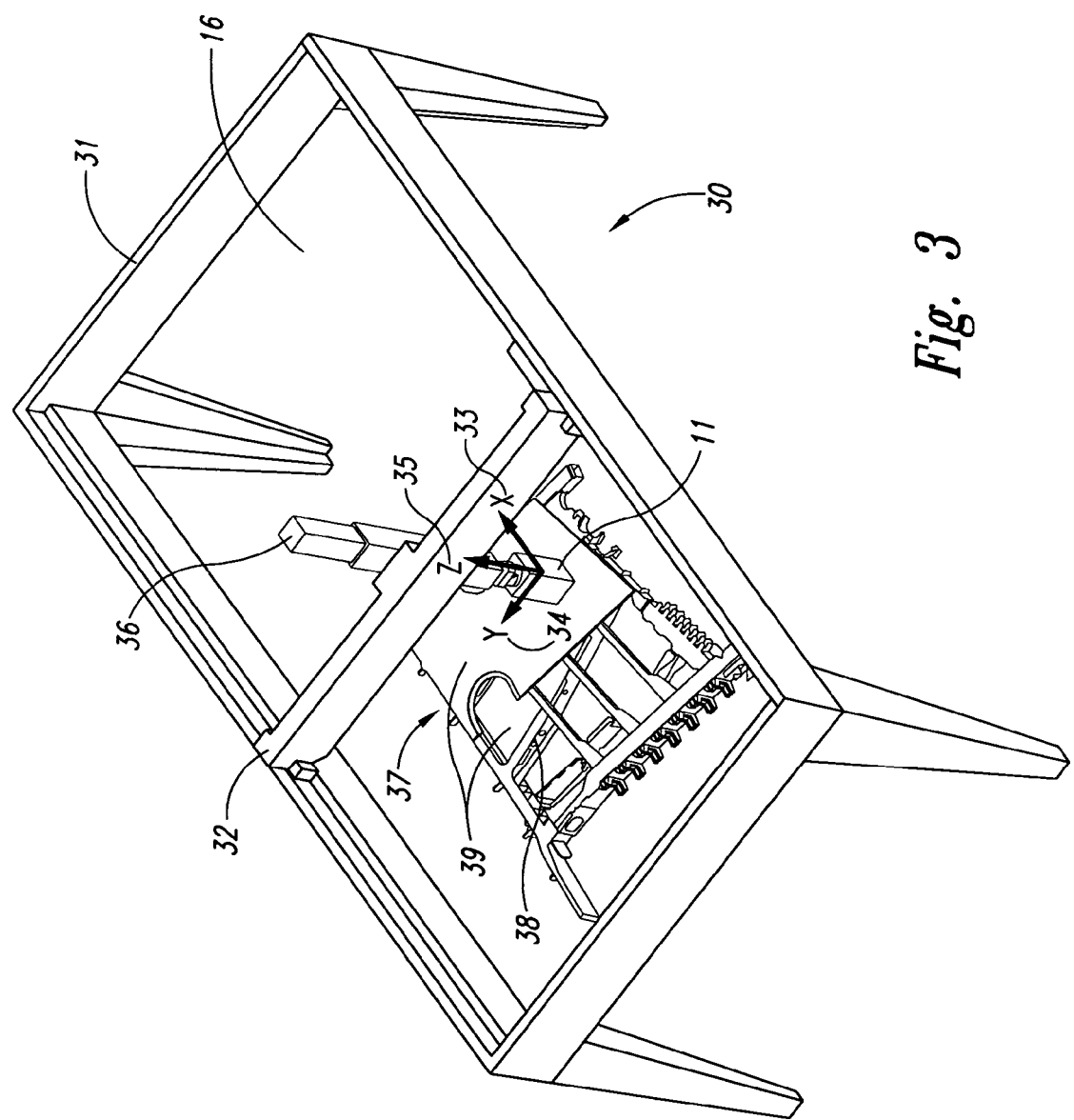
FIG. 3 is a perspective top view of a gantry motion system according to one embodiment of the present invention.
Figure 4:
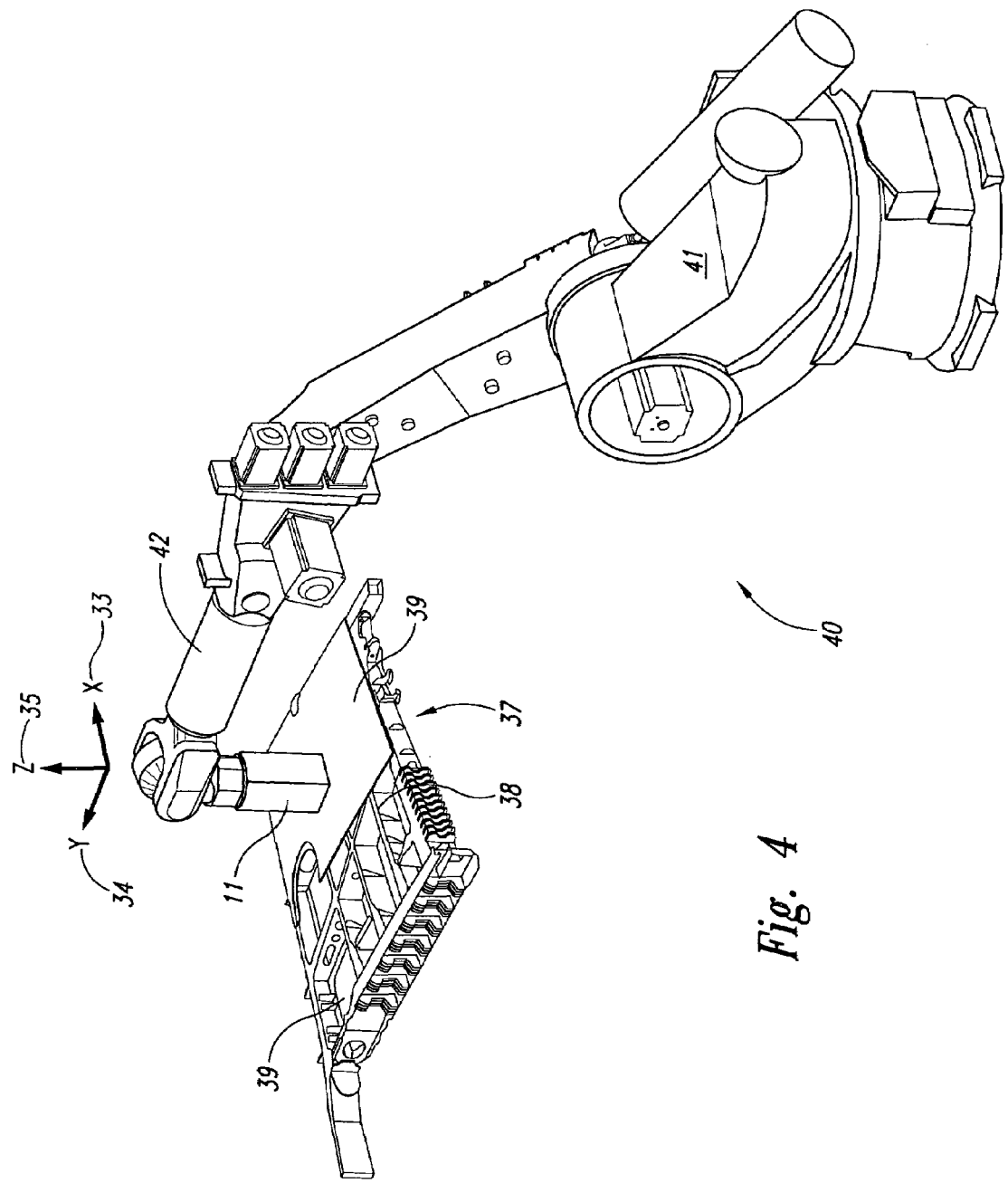
FIG. 4 is a perspective side view of a robot motion system according to one embodiment of the present invention.

Referring now to FIG. 1, a dependent scanning system 100 is illustrated according to one embodiment of the present invention. The dependent scanning system 100 may include a precision motion carriage 10, a probe 11, a controller box 17, and a computer interface 18. The dependent scanning system 100 may be used as a substructure scanning system. The dependent scanning system 100 may enable application of eddy current scanning with a high accuracy. The dependent scanning system 100 may be used as an attachment to an existing assembly machine, such as a machine executing numerically controlled operations, such as drilling, trimming, routing, machining or reaming. The assembly machine may locate the dependent scanning system 100 on a surface, for example, of a fuselage outer skin 31 (FIG. 3), where the dependent scanning system 100 may perform the final precision scan in an x (122)-y (132) raster mode. The precision motion carriage 10 may include a probe positioner 12, a probe positioner 13, and a frame 14. The frame 14 may have the shape of a square and may enclose a two-dimensional area 16. The probe positioner 12 may extend across the frame 14 in x-direction 122. The probe positioner 12 may include an opening 121 for guiding the probe 11. The probe positioner 12 may be inserted into the frame 14 such that it may be moved in y-direction 132, within the frame 14. The probe positioner 13 may extend across the frame 14 in y-direction 132. The probe positioner 13 may include an opening 131 for guiding the probe 11. The probe positioner 13 may be inserted in the frame 14 on top of the probe positioner 12 and in a right angle to the probe positioner 12. The probe positioner 13 may be moved in x-direction 122 within the frame 14. By positioning the probe positioner 13 over the probe positioner 12, the opening 131 and the opening 121 form a window 15. The probe 11 may be inserted in the window 15. Using the probe positioner 12 and the probe positioner 13, the probe 11 may be moved precisely over the area 16 enclosed by the frame 14. By inserting the probe 11 into the window 15, the probe 11 may be accurately indexed. The probe 11 may be moved to scan a two-dimensional area 16 in an x (122)-y (132) raster mode. The probe 11 may be further moved within the opening 121 in x-direction 122 for one-dimensional line scanning. The probe 11 may still further be moved within the opening 131 in y-direction 132 for one-dimensional line scanning. The probe 11 may be an eddy current scanning sensor that may be used to detect metallic features of a substructure 38 underneath an outer skin 39 (FIGS. 3 and 4), as frequently needed, for example, during the aircraft airframe assembly. The probe 11 may further be an ultrasonic scanning sensor that may be used to detect nonmetallic features of a substructure 38 underneath an outer skin 39 (FIGS. 3 and 4). The probe 11 may further be any nondestructive scanning sensor. Using the precision motion carriage 10 for scanning an assembly, such as test assembly 20 (FIGS. 2a and 2b) or the assembly 37 (FIGS. 3 and 4), may minimize changes in liftoff or fill factor resulting from probe 11 wobble or uneven surfaces, may provide repeatability of scanning results and high resolution mapping.

Figure 5:
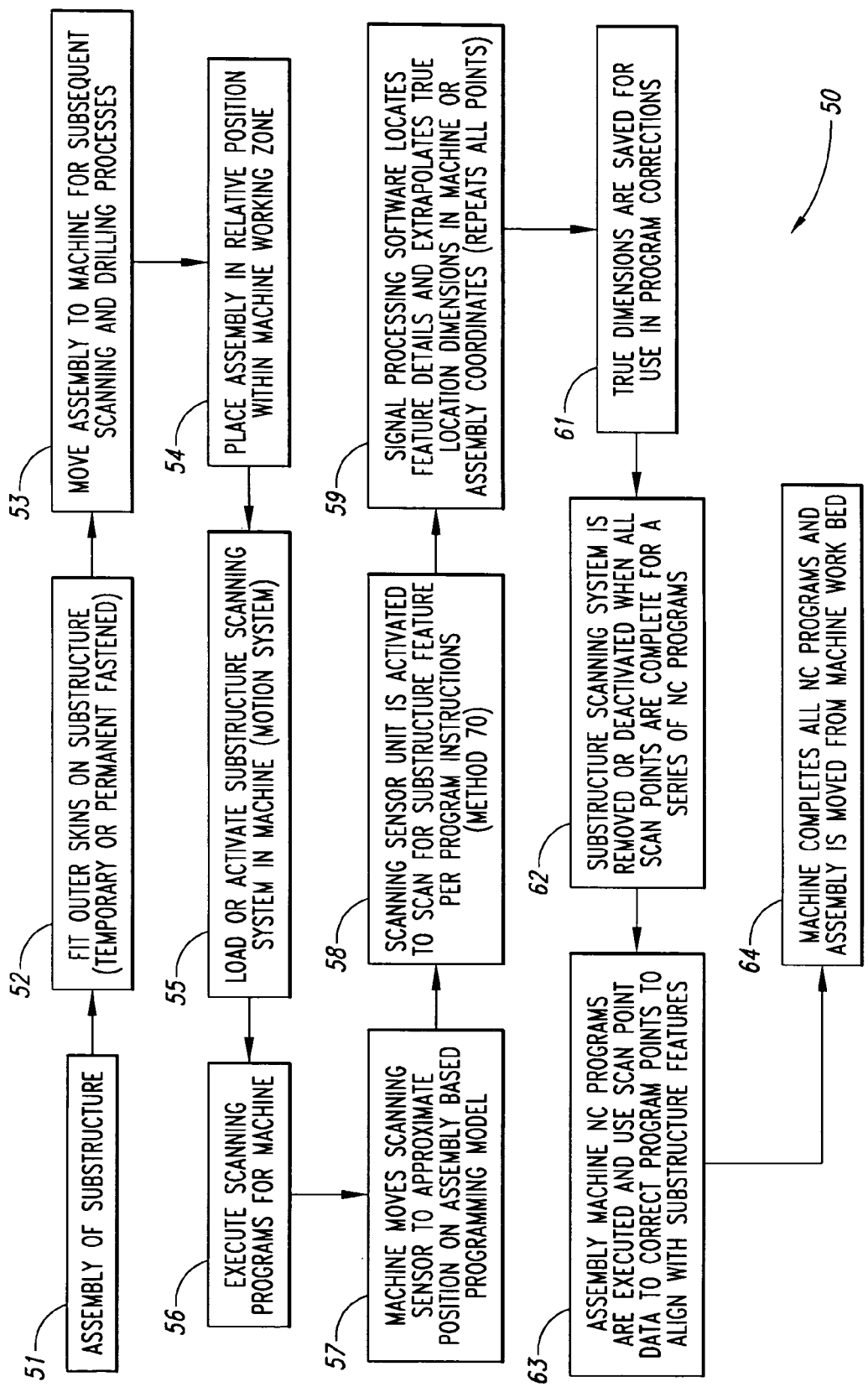
FIG. 5 is a flow chart of an assembly process according to another embodiment of the present invention.
Figure 6:
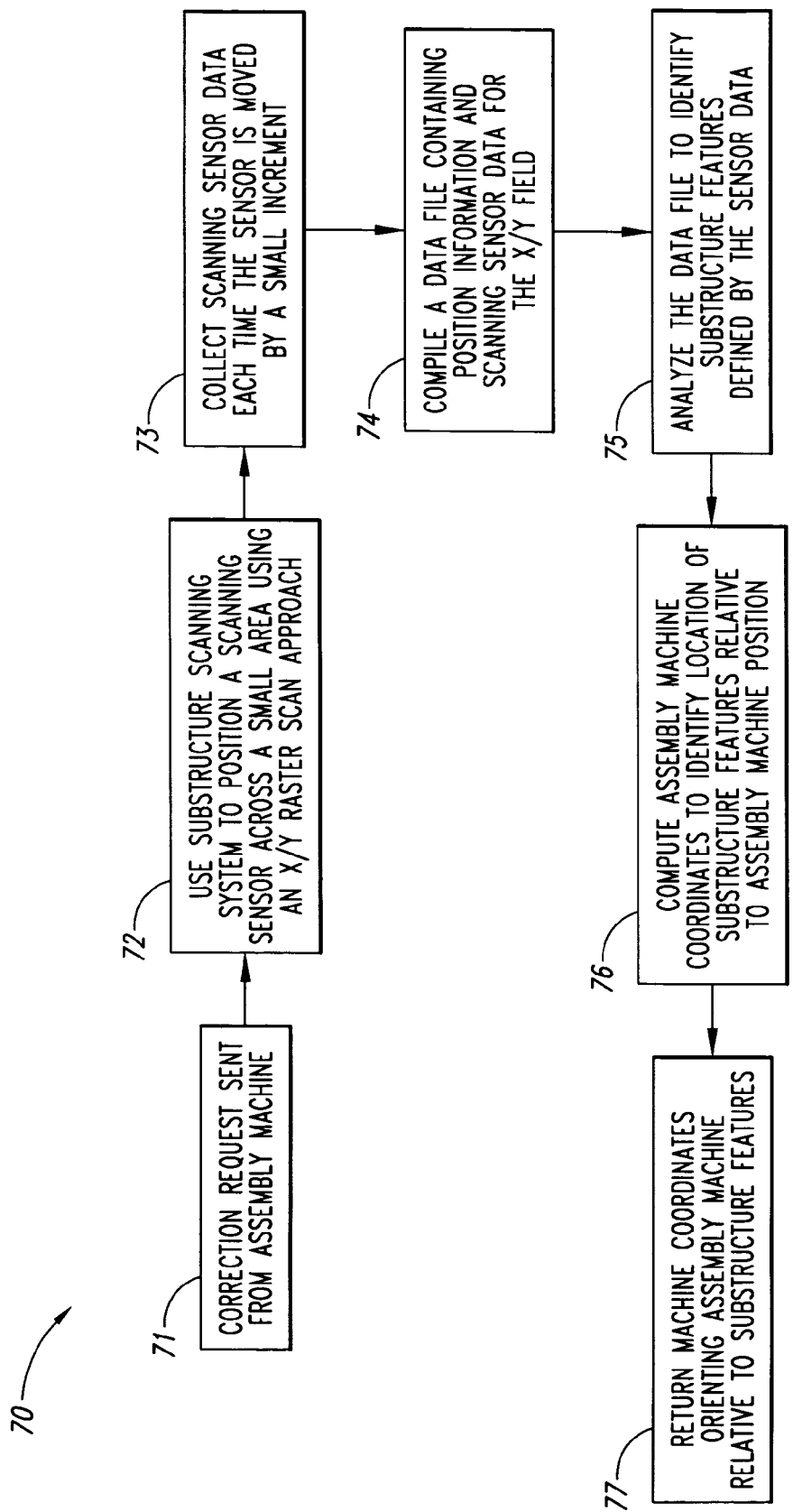
FIG. 6 is a flow chart of a method for machine coordinate correction according to another embodiment of the present invention.

As illustrated in FIG. 1, the probe 11 may be connected with a computer interface 18 via a controller box 17. The controller box 17 may provide an alternating current to the probe 11. The probe 11 may generate eddy currents and sense changes in the eddy current field. The controller box 17 may receive signals that indicate changes in the eddy current and supply these signals to the computer interface 18. The computer interface 18 may include scanning control software 181 and signal processing software 182. The computer interface 18 may be connected with a keyboard 183. The probe positioner 12 and the probe positioner 13 may be connected with the computer interface 18. The scanning control software 181 may control the movement of the probe positioner 12 and the probe positioner 13 and, therefore, of the probe 11. The signal processing software 182 may generate an image (such as the C-scan 25, FIG. 2c) of the substructure 38 (FIGS. 3 and 4). The signal processing software 182 may generate a C-scan 25 (as shown in FIG. 2c) if a two-dimensional area 16 was scanned in an x (122)-y (132) raster mode. The C-scan 25 may be a false-color plot of signal strength or phase angle shift as a function of the position of the probe 11. The signal processing software 182 may generate a strip chart if a line scan in x (122) or y (132) direction was done. Indications on the strip chart may be correlated to a position of the probe 11 and, therefore, to a position on the part being scanned. The scanning control software 181 and the signal processing software 182 may be integrated in numerically controlled machining programs (as shown in FIGS. 5 and 6).

Referring now to FIGS. 2a and 2b, a top view and a side view, respectively, of a test specimen 20 are illustrated according to one embodiment of the present invention. The test assembly 20 may include a panel 21 and a substructure 22. The substructure 22 may be smaller in size than the panel 21 and may include two holes 23. The substructure 22 may be positioned underneath the panel 21. The panel 21 may be the outer mold line skin of an aircraft fuselage or wing. The substructure 22 may be an edge of a flange of the substructure underneath the outer mold line skin or the wing including tooling holes.

Referring now to FIG. 2c, a C-scan 25 of the test assembly 20 (shown in FIGS. 2a and 2b) is illustrated according to one embodiment of the present invention. As can be seen, the substructure 22 including the holes 23 may be clearly and with precision identified in the C-scan 25. Used for the C-scan 25 were an aluminum skin 21, an aluminum rib 22, and an eddy current probe 11 (FIG. 1) operated at 3 kHz. The scanning parameters may be optimized according to the materials of the panel 21 and the substructure 23, by selecting, for example, an appropriate probe 11 (FIG. 1) and an appropriate scanning frequency.

Referring now to FIG. 3, a gantry motion system 30 is illustrated according to one embodiment of the present invention. The gantry motion system 30 may include a gantry 31, a bar 32, a pole 36, and a probe 11. The gantry motion system 30 may be used as a substructure scanning system. The gantry motion system 30 may provide precise positioning and movement of the probe 11 (also shown in FIG. 1). FIG. 1 shows the basic concept of precisely moving a probe 11 over an area 16 using a precision motion carriage 10. The same concept may be applied to the gantry motion system 30. The gantry 31 may be positioned over an assembly 37 to be scanned. The assembly 37 may include a substructure 38 and outer skins 39. The outer skins may be temporarily or permanently fastened to the substructure 38. The gantry 31 may cover a two-dimensional area 16. The bar 32 may be inserted into the gantry extending across the gantry 31 in y-direction 34 and being movable in x-direction 33. The pole 36 may be attached to the bar 32 such that the pole may move in y-direction 34 along the bar 32 and in z-direction 35. The pole 36 may include the probe 11 (also shown in FIG. 1). The probe 11 may be an eddy current scanning sensor that may be used to detect metallic features of a substructure 38 underneath an outer skin 39 as frequently needed, for example, during the aircraft airframe assembly. The probe 11 may further be an ultrasonic scanning sensor that may be used to detect nonmetallic features of a substructure 38 underneath an outer skin 39. The probe 11 may further be any nondestructive scanning sensor. The probe 11 may be facing the assembly 37. The probe 11 may be moved towards the assembly 37 and away from the assembly 37 by moving the pole 36 in z-direction 34. By moving the bar 32 in x-direction 33 and by moving the pole 36 in y-direction 34 along the bar 32, the probe 11 may be moved precisely over the outer skin 39 of the assembly 27. Consequently, the substructure 38 including all features, such as edges of flanges, machined steps, and tooling holes, may be located with high accuracy. The obtained location coordinates of the substructure 38 may be used to control subsequent assembly processes, for example, of an aircraft airframe, such as drilling, reaming, machining or routing. The obtained location coordinates of the substructure 38 may be provided to a numerically controlled assembly machine to correct machine coordinates according to the location of the substructure 38.

Referring now to FIG. 4, a robot motion system 40 is illustrated according to one embodiment of the present invention. The robot motion system 40 may include a robot 41 having a robot arm 42. A probe 11 (also shown in FIG. 1) may be attached to the robot arm 42. The probe 11 may be facing the assembly 37. The robot arm 42 may extend over an assembly 37 to be scanned. The robot arm 42 may position and move the probe 11 precisely over the outer skin 39 of the assembly 37 similar to the basic concept shown in FIG. 1 and as described above. The probe 11 may be an eddy current scanning sensor that may be used to detect metallic features of a substructure 38 underneath an outer skin 39 as frequently needed, for example, during the aircraft airframe assembly. The probe 11 may further be an ultrasonic scanning sensor that may be used to detect nonmetallic features of a substructure 38 underneath an outer skin 39 The probe 11 may further be any nondestructive scanning sensor. The robot motion system 40 may be used as a substructure scanning system.

The gantry motion system 30 and the robot motion system 40 may be examples for motion systems utilizing the basic concept of positioning and moving of a probe 11 as illustrated in FIG. 1 and as described above. In both Systems 30 and 40, the probe 11 may be connected with a computer interface 18 via a controller box 17 (as shown in FIG. 1). The controller box 17 may provide an alternating current to the probe 11, in the case, that the probe 11 is an eddy current scanning sensor. The probe 11 may generate eddy currents and sense changes in the eddy current field while being moved over the outer skin 39 of the assembly 37. The controller box 17 may receive signals that indicate changes in the eddy current and supply these signals to the computer interface 18. The computer interface 18 may include scanning control software 181 and signal processing software 182. The computer interface 18 may be connected with is connected with the controller box 17, the bar 32, and the pole 36. The scanning control software 181 may control the movement of the probe 11. The signal processing software 182 may generate images (such as the C-scan 25 shown in FIG. 2c) from the scanned area 16 (FIG. 1). Both, the gantry motion system 30 and the robot motion system 40 may be integrated in a machine executing numerically controlled operations, such as drilling, trimming, or reaming (as shown in FIGS. 5 and 6). This may improve the product flow and automation of assembly processes, such as the aircraft airframe assembly, as well as provide more flexibility of assembly processes.

Referring now to FIG. 5, a flow chart of an assembly process 50 is illustrated according to another embodiment of the present invention. The assembly process 50 may start with the assembly of a substructure 38 (shown in FIGS. 3 and 4) in step 51. In step 52, outer skins 39 may be fitted and fastened onto the substructure 38. The outer skins 39 may be temporary or permanently fastened to the substructure 38 forming the assembly 37 (shown in FIGS. 3 and 4). The assembly 37 may be moved to an assembly machine (step 53) and may be placed on the machine work bed in relative position within the machine work zone (step 54). In step 55, a substructure scanning system including a precision motion carriage 10 and a nondestructive scanning sensor 11 (FIG. 1), such as the gantry motion system 30 (FIG. 3) or the robot motion system 40 (FIG. 4), may be loaded in the machine and may be activated. The scanning control software 181 and the signal processing software 182 (FIG. 2) may be included in the interface of the assembly machine. In step 56, the scanning programs may be activated and executed by the substructure scanning system, for example, the gantry motion system 30 (FIG. 3) or the robot motion system 40 (FIG. 4). Step 56 may further include steps 57, 58, 59, and 61. The probe 11 that is operated as a scanning sensor may be positioned according to an assembly based programming model in step 57. The probe 11 may be activated and moved over the outer skin 39 of the assembly 37 (as shown in FIGS. 3 and 4) to scan for features of the substructure 38 per program instructions (step 58). The signal processing software 182 may locate feature details of the substructure 38 and may extrapolate the true location dimensions in machine or assembly 37 coordinates in step 59. All points may be scanned repeatedly to increase accuracy and scan point data may be collected and saved (step 59). The determined true dimensions of the substructure 38 features may be saved for use in program corrections of the assembly machine (step 61). When all scan points are completed for a series of numerically controlled programs, the substructure scanning system, for example, the gantry motion system 30 (FIG. 3) or the robot motion system 40 (FIG. 4), may be removed from the machine or deactivated in step 62. In Step 63, the numerically controlled programs for the assembly machine may be executed, for example, drilling, trimming, or reaming operations, while the scan point data may be used to correct program points and to align the assembly 37 and, therefore, the features of the substructure 38, relative to the machining tools. After the machine completes all numerically controlled programs in step 63, the assembly 37 may be moved from the machine work bed in step 64.

Referring now to FIG. 6, a flow chart of a method 70 for machine coordinate correction is illustrated according to another embodiment of the present invention. The method 70 may include the step of sending a correction request from an assembly machine (step 71). The assembly machine may be a numerically controlled assembly machine, for example, for the assembly of aircraft airframes. In step 72, a substructure scanning system, for example, the gantry motion system 30 (FIG. 3) or the robot motion system 40 (FIG. 4), may be used to position a probe 11 (FIGS. 3 and 4) on the outer skin 39 of an assembly 37 (FIGS. 3 and 4) and to move the probe 11 across a small area 16 (FIG. 1) using an x-y raster scan approach (FIGS. 1 and 3). The probe 11 may be a scanning sensor. The probe 11 may be any nondestructive inspection sensor. The probe 11 may be preferably an eddy current scanning sensor. The method 70 may further include the step of collecting scanning data each time the probe 11 is moved by a small increment (step 73). In step 74, a data file may be compiled containing position information and scanning data obtained with the probe 11 for the x-y field (area 16, FIG. 1). In the following step 75, the obtained data file may be analyzed to identify substructure 38 features defined by the sensor data. Step 76 may include computing assembly machine coordinates to identify location of substructure 38 features relative to assembly machine position. Machine coordinates orienting the assembly machine relative to the substructure 38 features may be returned in step 77. By applying the basic concept of the precision motion carriage 10 (as shown in FIG. 1) to substructure scanning systems, for example, the gantry motion system 30 (FIG. 3) or the robot motion system 40 (FIG. 4), using probes 11 for nondestructive scanning, features of substructure 38 (FIGS. 3 and 4) may be located with high accuracy meeting engineering tolerances. Furthermore, by using eddy current for detecting substructure the scanning may be performed through the outer skin 39 eliminating the steps of removing the outer skin, manually mapping the substructure 38, and refastening the outer skin 39 to the substructure. Even though the method for detecting substructure using precision eddy current scanning has been described mainly for application in the aircraft airframe assembly process, other applications, for example, in the automobile industry, may be possible.

It should be understood, of course, that the foregoing relates to exemplary embodiments of the invention and that modifications may be made without departing from the spirit and scope of the invention as set forth in the following claims.

We claim:

1. A method for detecting substructure, comprising the steps of:
   nondestructively scanning an assembly using a substructure scanning system including a precision motion carriage, a first probe positioner movably coupled to said precision motion carriage such that it can move in a first direction relative to said precision motion carriage, a second probe positioner located above said first probe positioner and movably coupled to said precision motion carriage such that it can move in a second direction relative to said precision motion carriage, and a nondestructive scanning sensor located in an opening of said first probe positioner and in an opening of said second probe positioner of said precision motion carriage;
   positioning said assembly including a substructure covered with an outer skin under said substructure scanning system;
   positioning said scanning sensor on said outer skin of said assembly;
   moving said scanning sensor over said outer skin with said first probe positioner and said second probe positioner of said precision motion carriage, wherein moving said scanning sensor is accomplished by moving said first probe positioner and/or said second probe positioner such that said scanning sensor moves within the opening of the first probe positioner and/or within the opening of the second probe positioner;
   locating said substructure through said outer skin by evaluating signals received from said scanning sensor; and
   controlling an assembly process using said location of said substructure.

2. The method for detecting substructure of claim 1, further comprising the steps of:
   nondestructively scanning said assembly using an eddy current scanning sensor; and
   detecting metallic features of said substructure.

3. The method for detecting substructure of claim 1, further comprising the steps of:
   nondestructively scanning said assembly using an ultrasonic scanning sensor; and
   detecting nonmetallic features of said substructure.

4. The method for detecting substructure of claim 1, further comprising the step of:
   scanning a two-dimensional area of said outer skin in an x-y raster mode with said scanning sensor.

5. The method for detecting substructure of claim 1, further comprising the step of:
   line scanning said outer skin in one dimension with said scanning sensor.

6. The method for detecting substructure of claim 1, further comprising the steps of:
   connecting said scanning sensor with a controller box;
   connecting said controller box with a computer interface;
   feeding an alternating current to said scanning sensor using said controller box;
   generating an eddy current with said scanning sensor;
   sensing changes in the eddy current field with said scanning senor;
   receiving signals indicating said changes in the eddy current field with said controller box; and
   supplying said signals to said computer interface with said controller box.

7. The method for detecting substructure of claim 6, further comprising the steps of:
   controlling the position and movement of said scanning sensor with scanning control software included in said computer interface; and
   generating an image of said substructure using signal processing software included in said computer interface.

8. The method for detecting substructure of claim 1, further comprising the step of:
   integrating said substructure scanning system into a numerically controlled assembly machine.

9. The method for detecting substructure of claim 1, further comprising the step of:
   scanning for said substructure using a gantry motion system.

10. The method for detecting substructure of claim 1, further comprising the step of:
    scanning for said substructure using a robot motion system.

* * * * *